United States Patent

Jochems et al.

Patent Number: 6,058,204
Date of Patent: *May 2, 2000

[54] PROCESS FOR THE AUTOMATIC DETECTION OF DEFECTS IN MECHANICAL PARTS HAVING COMPLEX GEOMETRY

[75] Inventors: Tilman Jochems, Perpignan; Véronique Hélène Marie Pierre Prejean-Lefevre, Sceaux, both of France

[73] Assignee: Societe Nationale d'Etude et de Moteurs d'Aviation "Snecma", Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/914,214

[22] Filed: Aug. 19, 1997

[30] Foreign Application Priority Data

Aug. 29, 1996 [FR] France .................................. 96 10552

[51] Int. Cl.$^7$ ....................................................... G06K 9/00
[52] U.S. Cl. ............................................. 382/152; 382/257
[58] Field of Search ..................................... 382/132, 152, 382/256, 257; 364/551.02; 348/180, 192, 221, 254

[56] References Cited

FOREIGN PATENT DOCUMENTS

| 0 375 157 | 6/1990 | European Pat. Off. . |
| 0 576 961 | 1/1994 | European Pat. Off. . |
| 0 599 335 | 6/1994 | European Pat. Off. . |

*Primary Examiner*—Amelia Au
*Assistant Examiner*—Samir Ahmed
*Attorney, Agent, or Firm*—Oblon, Spivak, McClelland, Maier & Neustadt, P.C.

[57] ABSTRACT

A process for the automatic detection of defects in a complexe part comprises segmenting a radioscopic image of the part into two classes of zone in such a way as to obtain a binary images referred to as a mask, in which the assessable zones and the non-assessable zones respectively assume the values 1 and 0, and applying to the radioscopic image conditional morphological transformations formulated from a conditional formative element obtained by intersection between a conventional formative element and the mask. The process is particularly applicable to the radioscopic inspection and evaluation of blade castings.

4 Claims, 3 Drawing Sheets

PROCESS FOR THE AUTOMATIC DETECTION OF DEFECTS IN MECHANICAL PARTS HAVING COMPLEX GEOMETRY

BACKGROUND OF THE INVENTION

1. Field of the Invention

The invention relates to a process for the automatic detection of defects in mechanical parts of complex geometry by inspection of a radioscopic image of the part, and is particularly applicable in the field of aeronautics to the automatic appraisal of blade castings which are inspected radioscopically.

2. Summary of the Prior Art

Non-destructive radioscopic inspection has hitherto been limited to the checking of parts having a simple geometry. For parts of this type, the radioscopic images comprise assessable zones of homogenous appearance in which the variations in the grey levels are of the low frequency type and in which possible defects are looked for after the employment of image processing operations such as morphological transformations and linear filtering.

These image processing operations are determined from standard formative elements of predetermined size and shape and assume that the assessable zones of the image are infinite wholes, all the points of the image having the same number of adjacent points (this condition is not in fact true at the limits of the assessable zones).

In the case of parts with complex geometry the radioscopic image has a texture including zones of low contrast which are bereft of useful information and which constitute non-assessable zones. These non-assessable zones are superimposed on the assessable zones of the image, and the application of conventional image processing operations gives erroneous results due to the effect of the zones which are devoid of useful data. The low contrast or saturated zones in fact represent discontinuities in the assessable zones, which can no longer be regarded as infinite wholes.

It is an object of the invention therefore to provide a process for the automatic detection of defects which can be applied to parts of complex geometry, whose radioscopic image comprises assessable zones having a gradient of grey levels and on which saturated zones which are very light or very dark and comprise no useful data are superimposed.

SUMMARY OF THE INVENTION

For this purpose the invention proposes to apply to the radioscopic image of a complex part novel image processing operations, the result of which depends solely on the points of the image situated in the assessable zones of the image. These new operations comprise segmenting the radioscopic image into two classes of zone in order to obtain a binary image, referred to as a mask, in which the assessable zones and the non-assessable zones respectively assume the values 1 and 0, and then applying to the radioscopic image conditional morphological transformations formulated from a conditional formative element which is obtained by intersection between a conventional formative element and the mask.

More particularly, according to the invention there is provided a process for the automatic detection of defects in a mechanical part of complex geometry from a radioscopic image of the part having zones bereft of useful data, referred to as non-assessable zones, within so-called assessable zones, comprising the steps of:

producing at least one radioscopic image of the part to be inspected;

segmenting the radioscopic image into two classes of zones corresponding respectively to the assessable zones and the non-assessable zones in order to obtain a binary image referred to as a mask;

choosing a standard formative element of predetermined size and shape;

defining a conditional formative element equal to the intersection of the standard formative element with the mask;

defining conditional morphological transformations using the conditional formative element; and applying the said conditional morphological transformations to the radioscopic image in such a way as to show up possible defects in the assessable zones of the image.

Preferred features and advantages of the invention will become apparent from the following description of a preferred embodiment, given by way of non-limitative example, with reference to the accompanying drawings.

DESCRIPTION OF THE PREFERRED EMBODIMENT

Figure 1:
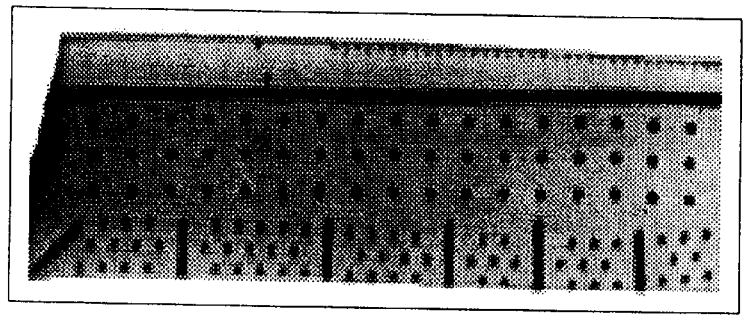
FIG. 1 shows an example of a radioscopic image of a hollow blade casting.

FIG. 1 shows an example of a radioscopic image of a hollow blade having internal structures such as baffles and walls. These are superposed on the assessable zone to be inspected and form areas of low contrast which are bereft of useful data in the image. These regions appear in black in the radioscopic image of the hollow blade shown in FIG. 1 and constitute zones which cannot be assessed.

Furthermore, as the hollow blade does not have a uniform thickness, the radioscopic image exhibits a gradient of grey levels in the assessable zone.

Figure 2:
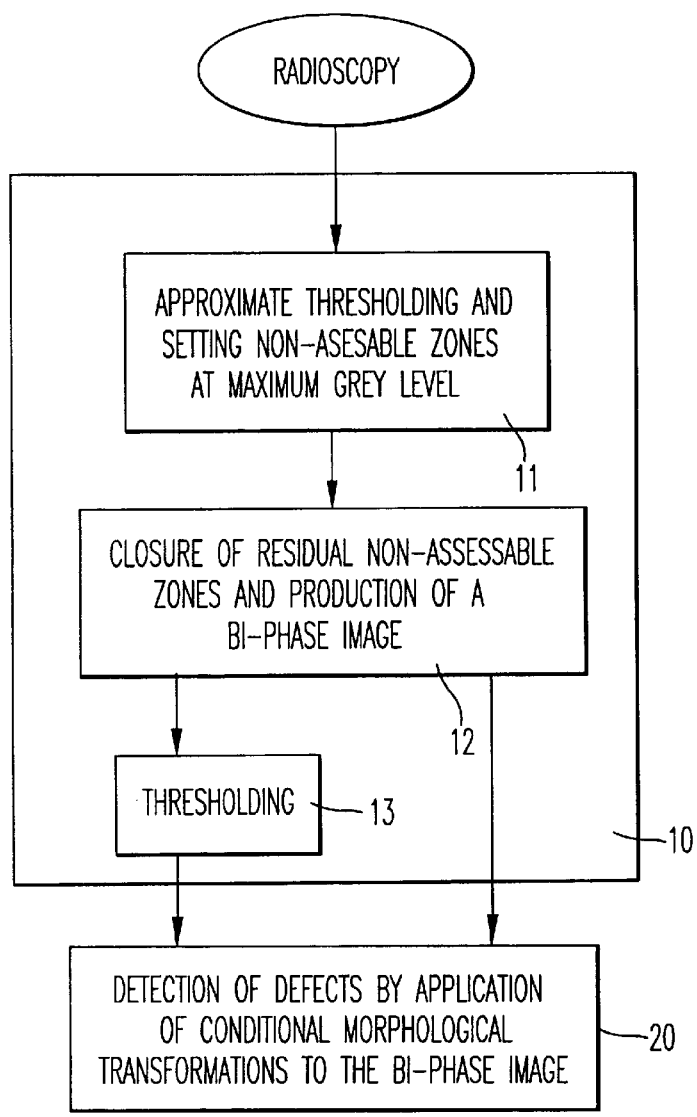
FIG. 2 is a flow chart diagram of the main stages of the defect detection process in accordance with the invention.

FIG. 2 shows a chart of the main stages in the process in accordance with the invention for detecting defects in a complex mechanical part using a radioscopic image of the part.

In a first stage 10, the radioscopic image of the part is segmented into two classes of zones, these two classes corresponding respectively to the homogenous assessable zones and to the non-assessable zones. The result of the segmentation is expressed in the form of a binary image, referred to as a mask in which the two classes of zone are represented by binary values equal to 0 and 1. For example, the value 1 is attributed to the points of the image which belong to an assessable zone, and the value 0 is attributed to the points of the image which correspond to the non-assessable zones. Segmentation of the radioscopic image is carried out in a number of successive sub-stages. The first sub-stage 11 consists of carrying out an approximate thresholding of the radioscopic image in order to select the points of the image which without any doubt belong to the regions bereft of useful data and to allocate to these points a predetermined grey level value.

The grey level value is chosen so that it cannot be confused with the useful data. For example, the value 255 which corresponds to saturated white may be chosen since this value cannot represent useful data. In the event of the radioscopic image exhibiting a substantial gradient of grey levels in the assessable zone, the sub-stage 11 may be preceded by a preliminary operation to restore the background of the assessable zone to flatness. This preliminary operation may, for example, be a so-called "top hat" transformation or a low pass filter.

After the thresholding has been carried out approximately, the points of the image which belong to the regions devoid of useful data are not all set at a value of 255, and residual non-assessable zones which are of very small size remain situated around those zones to which the value 255 has been given.

Figure 4:
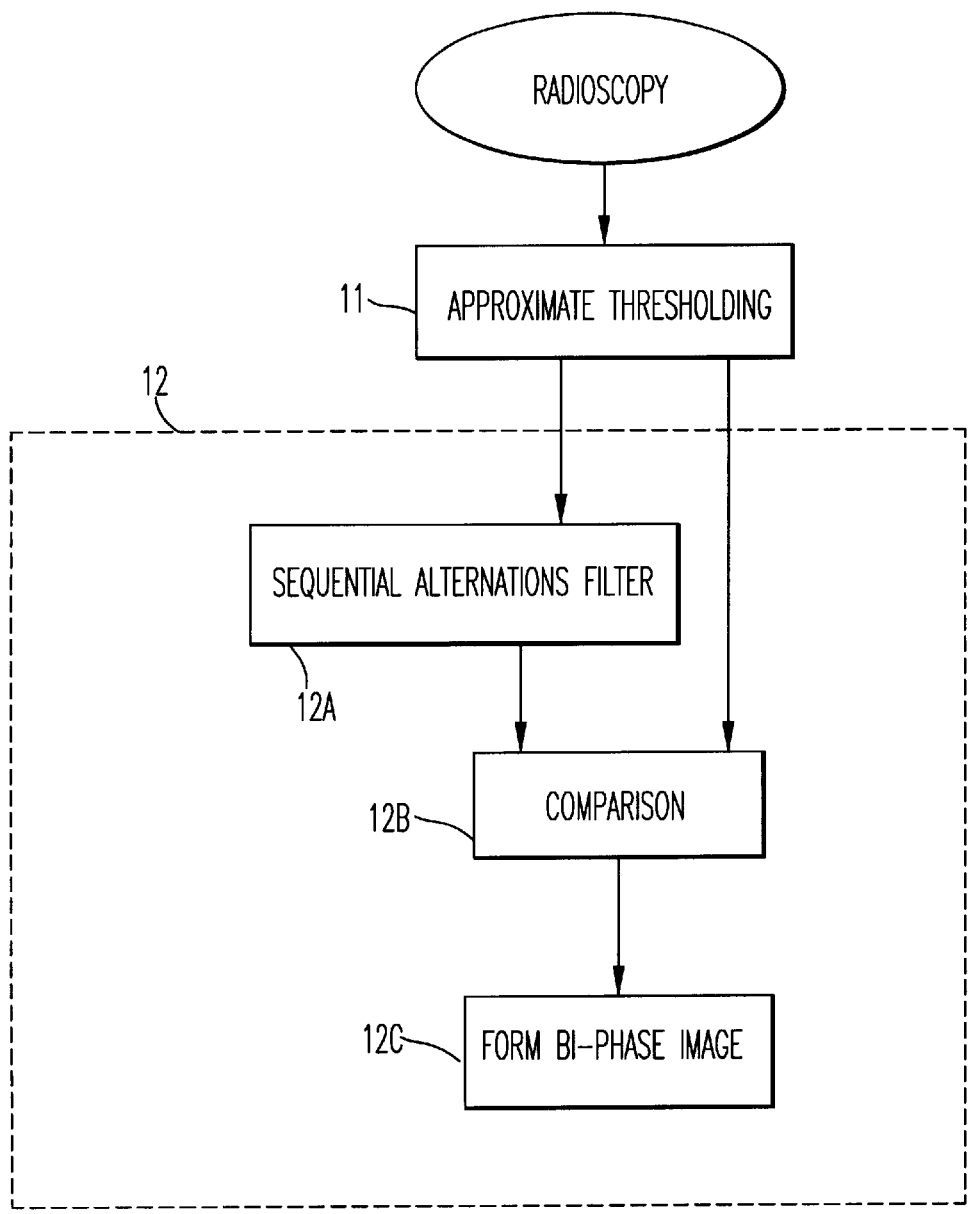
FIG. 4 is a flowchart diagram of the sub-stages of the production of a bi-phase image.

In a second sub-stage 12 these residual zones of small size are closed employing a closure operation further sub-stages as illustrated in FIG. 4, in which at least one sequential alternating filter (12A) is applied to the image obtained in sub-stage 11. In the event of the image exhibiting defects of a size smaller than or equivalent to the size of the non-assessable residual zones, the application of the sequential alternating filter (12A) may be followed by a defect recovery operation consisting of comparing (12b) the images obtained before (from 11) and after application of the sequential alternating filter (12A) and giving each point of the image the maximum grey level value associated with this point in one or other of these images. When the non-assessable residual zones are closed, the image obtained is a bi-phase image (12c) in which grey level values represent the assessable zones and the non-assessable zones of the radioscopic image, the non-assessable zones having a grey level equal to a predetermined value, for example 255. This bi-phase image is then thresholded in a third sub-stage 13 in order to obtain a binary image in which the assessable zones and the non-assessable zones respectively assume the binary values 1 and 0. This binary image constitutes a mask from which a conditional formative or structuring element is defined, along with conditional morphological transformations. This mask is then given the form of a digital image in grey levels by means of multiplication by the value 255 corresponding to the maximum value of an image in grey levels.

Figure 3:
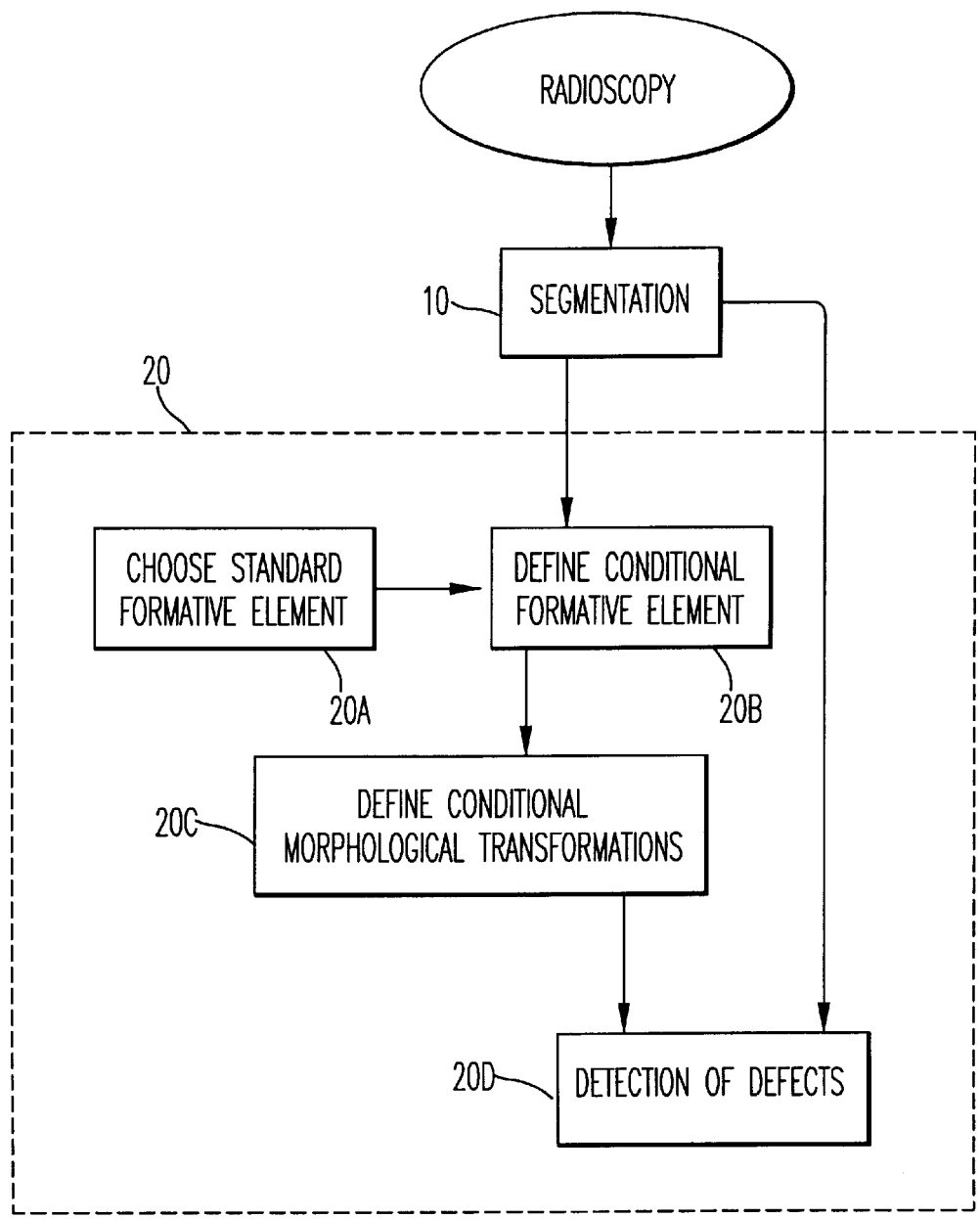
FIG. 3 is a flowchart diagram showing sub-stages of the defect detection process in accordance with the invention.

In a second stage 20, as shown in detail in FIG. 3, conditional morphological transformations are (20c) formulated and applied along with the bi-phase image obtained from segmentation sub-stage 12 in order to detect possible defects (20d). The conditional morphological transformations (20c) are formulated by replacing a chosen standard formative element (20A) in the expressions of conventional morphological transformations by a conditional formative element (20b). This conditional formative element (20b) is obtained by producing an intersection between the chosen standard formative element (20A) and the mask obtained from 10, and makes it possible to take into account configurations of the vicinity in which the number of neighbouring members is not constant. The conditional formative element is of the same size as the chosen standard formative element (20A) but makes it possible to take into account only those points belonging to the assessable zones of the image.

When the conditional morphological transformations (20c) are applied to binary images, these images are considered as wholes and the transformations give rise to intersection and union operations in which the mask acquires a binary form. For example, the conditional morphological expansion of a binary image X is the whole of the origins y of all the conditional formative elements transferred to the image X, whose intersection with the image X is not empty. Since the conditional formative element is obtained by an intersection with the mask, the result of conditional expansion does not depend upon points of the image situated in non-assessable zones.

Considering the properties of intersections between wholes, the conditional morphological expansion of the image X may also be obtained by producing an intersection between the binary image X and the mask and then applying to the result of this intersection a conventional morphological expansion.

Similarly, the conditional morphological erosion of a binary image X is the whole of the origins y of all the transferred conditional formative elements which are completely included in the image X. Considering the properties of intersections and unions between wholes, the conditional morphological erosion of a binary image X may also be obtained by bringing about a union between the binary image X and the complement of the mask, then applying a conventional morphological erosion to the result of this union.

In the same way, a conditional morphological opening or a conditional morphological closure is formulated by using a conditional formative element. Considering the properties of the intersections and unions between wholes, the conditional morphological opening may also be obtained by making a union between the binary image X and the complement of the mask, then applying a conventional morphological opening to the result of this union, followed by an intersection of the result of the opening with the mask. In a similar manner, the conditional morphological closure may be obtained by producing an intersection between the binary image X and the mask, then applying a conventional morphological closure to the result of this intersection followed by a union of the result of the closure with the complement of the mask.

More complex transformations such as sequential alternating filters or the gradient are obtained in a similar manner by using combinations of the transformations which are explained above.

As for conventional morphological transformations, the conditional transformations may be generalised as digital images in terms of grey levels. In this case, the mask is, an image on which the points which belong to a non-assessable zone assume the maximum value in terms of grey levels, the other points of the image assuming a zero value. The intersection and union operations are respectively replaced by the minimum and maximum functions between two digital images.

The invention is not limited to the embodiment which has been described above. In particular it is also applicable to cases in which zones bereft of useful data appear as very light zones by employing the duality principle whereby the operations of morphological closure are replaced by morphological opening operations and vice versa, and likewise, the operations of morphological erosion are replaced by operations of morphological expansion. On the other hand, when the zones which have no useful data are very light zones, the recovery of defects after application of a sequential alternating filter to the radioscopic image is carried out by attributing to each point of the image the minimum grey level value associated with it in the image prior to or after filtering.

We claim:

1. A process for the automatic detection of defects in a mechanical part of complex geometry from a radioscopic image of said part having zones bereft of useful data, referred to as non-assessable zones, within assessable zones, comprising:

producing at least one radioscopic image of the mechanical part to be inspected;

segmenting said radioscopic image into two classes of zones corresponding respectively to said assessable zones and said non-assessable zones in order to obtain a bi-phase radioscopic image in which different values of gray levels represent the assessable zones and the non-assessable zones and processing said values of gray levels to obtain a binary image referred to as a mask;

choosing a standard formative element of predetermined size and shape;

calculating the intersection of said standard formative element with said mask;

modifying the standard formative element based on the calculated intersection of said standard formative element with said mask to generate a modified formative element;

defining conditional morphological transformations using said modified formative element; and applying said conditional morphological transformations to said bi-phase radioscopic image in such a way as to show possible defects in the assessable zones.

2. The process according to claim 1, wherein said step of segmenting said radioscopic image comprises a first stage of carrying out an approximate thresholding of said radioscopic image so as to select the points of the radioscopic image which undoubtedly belong to said non-assessable zones and allocating to these points a predetermined grey level value; a second stage of closing the residual non-assessable zones situated in the vicinity of the selected points in such way as to obtain the bi-phase radioscopic image; and a third stage of thresholding said bi-phase radioscopic image obtained in said second stage in order to obtain said binary image constituting said mask.

3. The process according to claim 2, wherein said second stage of closing the residual non-assessable zones comprises applying to the radioscopic image at least one sequential alternating filter, comparing radioscopic images obtained before and after application of said sequential alternating filter, and attributing to each point of the radioscopic image the maximum grey level value associated with this point in one of the radioscopic images obtained before and after application of said sequential alternating filter.

4. The process according to claim 2, wherein the applying of said conditional morphological transformations includes applying a conditional morphological opening or a conditional morphological closing.

* * * * *